(12) United States Patent
Haslbeck et al.

(10) Patent No.: US 12,171,980 B2
(45) Date of Patent: Dec. 24, 2024

(54) MEDICAL FLUID-LINE ARRANGEMENT AND MEDICAL ELASTOMERIC PUMP HAVING SUCH A FLUID-LINE ARRANGEMENT

(71) Applicant: B. Braun Melsungen AG, Melsungen (DE)

(72) Inventors: Karsten Haslbeck, Melsungen (DE); Jens Wildhagen, Hannover (DE)

(73) Assignee: B. Braun Melsungen AG, Melsungen (DE)

( * ) Notice: Subject to any disclaimer, the term of this patent is extended or adjusted under 35 U.S.C. 154(b) by 677 days.

(21) Appl. No.: 17/420,793

(22) PCT Filed: Nov. 6, 2019

(86) PCT No.: PCT/EP2019/080402
§ 371 (c)(1),
(2) Date: Jul. 6, 2021

(87) PCT Pub. No.: WO2020/143940
PCT Pub. Date: Jul. 16, 2020

(65) Prior Publication Data
US 2022/0072223 A1 Mar. 10, 2022

(30) Foreign Application Priority Data
Jan. 10, 2019 (DE) ................ 10 2019 200 253.6

(51) Int. Cl.
*A61M 5/145* (2006.01)
*A61M 5/14* (2006.01)
(Continued)

(52) U.S. Cl.
CPC ........ *A61M 5/14586* (2013.01); *A61M 5/141* (2013.01); *A61M 5/152* (2013.01);
(Continued)

(58) Field of Classification Search
CPC .............. A61M 5/14586; A61M 5/141; A61M 5/152; A61M 5/16804; A61M 5/44
(Continued)

(56) References Cited

U.S. PATENT DOCUMENTS 3,612,059 A * 10/1971 Ersek ..................... A61M 5/44
604/113
2013/0123728 A1 5/2013 Pratt et al.
(Continued)

FOREIGN PATENT DOCUMENTS

CN 103874519 A 6/2014
CN 106999650 A 8/2017
(Continued)

OTHER PUBLICATIONS

Office Action received in Chinese Application No. 201980088529.4 dated Mar. 1, 2023, with translation, 17 pages.
(Continued)

*Primary Examiner* — Phillip A Gray
(74) *Attorney, Agent, or Firm* — Christopher A. Rothe; CM Law

(57) ABSTRACT

A medical fluid-line arrangement and a medical elastomeric pump having such a fluid-line arrangement. The fluid-line arrangement transfers a medical fluid between a medical elastomeric pump and a patient port. The fluid-line arrangement has a fluid-line channel with an inlet and an outlet. The inlet connects to an outlet of the elastomeric pump, and the outlet connects to the patient port. A throttle element is connected in a fluid-conducting manner to the inlet and outlet of the fluid-line channel. A portion of the fluid-line channel extends through the throttle element. The throttle element causes a narrowing of an active-flow cross section of the fluid-line channel. The throttle element is encapsulated at least partially in a thermally conductive body having a heat-absorption surface that is larger than an outer surface of the throttle element and that is intended to be applied flat to a skin surface of a patient.

16 Claims, 3 Drawing Sheets

(51) Int. Cl.
*A61M 5/152* (2006.01)
*A61M 5/168* (2006.01)
*A61M 5/44* (2006.01)

(52) U.S. Cl.
CPC .......... *A61M 5/16804* (2013.01); *A61M 5/44* (2013.01); *A61M 2205/0233* (2013.01); *A61M 2205/3334* (2013.01); *A61M 2205/3355* (2013.01); *A61M 2205/3613* (2013.01)

(58) Field of Classification Search
USPC .......................................................... 604/132
See application file for complete search history.

(56) References Cited

U.S. PATENT DOCUMENTS

| | | |
|---|---|---|
| 2017/0000945 A1 | 1/2017 | Haslbeck |
| 2017/0259014 A1 | 9/2017 | Nessel |
| 2018/0280610 A1 | 10/2018 | Stettner |

FOREIGN PATENT DOCUMENTS

| | | |
|---|---|---|
| DE | 4241830 A1 | 6/1994 |
| DE | 4444180 A1 | 6/1995 |
| EP | 3096818 A1 | 11/2016 |
| EP | 3381489 A1 | 10/2018 |
| ES | 2167281 A1 | 5/2002 |
| GB | 317213 A | 8/1929 |
| WO | 8603978 A1 | 7/1986 |
| WO | 2014072079 A1 | 5/2014 |
| WO | 2015110387 A1 | 7/2015 |

OTHER PUBLICATIONS

Search Report received in German Application No. 10 2019 200 253.6 dated Sep. 26, 2019, with translation, 16 pages.
Search Report received in International Application No. PCT/EP2019/080402 dated Dec. 13, 2019, with translation, 4 pages.
Written Opinion received in International Application No. PCT/EP2019/080402 dated Dec. 13, 2019, with translation, 13 pages.
Office Action received in Chinese Application No. 201980088529.4 dated Oct. 12, 2023, with translation, 19 pages.

* cited by examiner

MEDICAL FLUID-LINE ARRANGEMENT AND MEDICAL ELASTOMERIC PUMP HAVING SUCH A FLUID-LINE ARRANGEMENT

CROSS-REFERENCE TO RELATED APPLICATION(S)

This application is the United States national phase entry of International Application No. PCT/EP2019/080402, filed Nov. 6, 2019, and claims the benefit of priority of German Application No. 10 2019 200 253.6, filed Jan. 10, 2019. The contents of International Application No. PCT/EP2019/080402 and German Application No. 10 2019 200 253.6 are incorporated by reference herein in their entireties.

FIELD

The invention relates to a medical fluid-line arrangement for transferring a medical fluid in a fluid-conveying manner between a medical elastomeric pump and a patient port, the fluid-line arrangement having a fluid-line channel with an inlet, which is provided for connection in a fluid-conducting manner to an outlet of the elastomeric pump, and an outlet, which is provided for connection in a fluid-conducting manner to the patient port, and a throttle element, which is connected in a fluid-conducting manner to the inlet and to the outlet of the fluid-line channel and through which a portion of the fluid-line channel extends, wherein the throttle element causes a partial narrowing of an flow-active cross section of the fluid-line channel.

The invention further relates to a medical elastomeric pump for delivering a medical fluid, with an elastomeric membrane which forms a pump volume for receiving and delivering the medical fluid, wherein the elastomeric membrane is elastically expanded in a filling state at least partially filled with the medical fluid and exerts an expansion-induced delivery pressure on the pump volume, and wherein a volumetric flow of the medical fluid can be delivered through an outlet of the pump volume by means of the delivery pressure.

BACKGROUND

A medical elastomeric pump of this kind and a medical fluid-line arrangement of this kind are generally known in the field of medicine and are provided for use in infusion therapy. Such elastomeric pumps have an elastomeric membrane which forms a pump volume for receiving and delivering a medical fluid that is to be administered in the context of the infusion therapy. During filling of the pump volume with the medical fluid, the membrane is elastically expanded like a balloon. The membrane expanded in this way exerts a delivery pressure on the pump volume. The known medical fluid-line arrangement serves for transferring the medical fluid in a fluid-conveying manner from the medical elastomeric pump to a patient port. Such fluid-line arrangements usually have a fluid-line channel which, at the inlet end, is connected in a fluid-conducting manner to an outlet of the pump volume. At the outlet end, the fluid-line channel is connectable in a fluid-conducting manner to the patient port. The known fluid-line arrangement has a hose-shaped configuration and can also be designated as a transfer system. To achieve correct dosing of the medical fluid, the fluid-line arrangement usually has a throttle element, which can also be designated as a flow limiter. The throttle element forms a partial narrowing of the fluid-line channel. This narrowing causes a throttling of the volumetric flow of the medical fluid delivered through the fluid-line channel by means of the elastomeric pump.

SUMMARY

The object of the invention is to make available a medical fluid-line arrangement and a medical elastomeric pump which are of the type mentioned at the outset and which permit improved dispensing of the medical fluid. It is in particular the object of the invention to permit delivery and/or transfer of the medical fluid in a way that is as robust as possible with respect to external influences.

For the fluid-line arrangement, this object is achieved by the fact that the throttle element is encapsulated at least partially in a thermally conductive body, which has a heat-absorption surface that is larger than an outer surface of the throttle element and that is intended to be applied flat to a skin surface of a patient. The invention proceeds from the consideration that the action of the throttle element, hence ultimately the dispensing of the medical fluid, depends in particular on a viscosity of the medical fluid. The viscosity is in turn dependent in particular on a temperature of the medical fluid. This temperature is in turn influenced by external factors, such as an ambient temperature, and a temperature of components of the fluid-line arrangement that convey fluid. These factors are naturally subject to certain fluctuations. The solution according to the invention makes it possible to counteract undesired effects of these fluctuations on the action of the throttle element and thus on the dispensing of the medical fluid. The fluid-line arrangement, at any rate when the heat-absorption surface is applied to the skin surface, ensures that the temperature of the throttle element is as constant as possible. To this extent, the thermally conductive body serves as a kind of heat exchanger between the skin surface of the patient and the throttle element. By virtue of the heat-absorption surface being larger than the outer surface of the throttle element, an improved heat transfer between the skin surface and the outer surface of the throttle element can be achieved. This heat transfer counteracts the throttle action being influenced by external temperature fluctuations. The solution according to the invention thus allows the medical fluid to be dispensed in a way that is as robust as possible with respect to external influences. The fluid-line channel extends partially upstream and partially downstream of the throttle element and also partially through the throttle element. The fluid-line channel can in particular be formed by hose-shaped or tubular fluid-line portions. The fluid-line channel is preferably formed of flexible hose portions which are made from plastic and which can be produced in one continuous piece and/or can be produced separately and thereafter joined together in a fluid-conducting manner. The inlet of the fluid-line channel can have a connector for releasable connection to the outlet of the medical elastomeric pump. Alternatively, the inlet can be provided for non-releasable fluid-conducting connection to the outlet of the elastomeric pump. The outlet of the fluid-line channel preferably has a connector for releasable fluid-conducting connection to the patient port. The throttle element can be designed in the form of a flow throttle, a diaphragm or the like. Preferably, the throttle element has a capillary-like passage which causes the partial narrowing of the fluid-line channel for throttling the medical fluid. The capillary-like passage can also be designated as a capillary and, in relation to the active-flow cross section of the rest of the fluid-line channel, can have an active-flow cross section that is smaller by at least one order of magnitude, preferably at least two orders of magnitude. Preferably, in relation to a fluid resistance of the rest of the fluid channel, the throttle element has a fluid resistance that is greater by at least one order of magnitude, preferably at least two orders of magnitude. The throttle element can in particular be hose-shaped or tubular. The throttle element can be made from plastic or glass, for example. The throttle element preferably has a circular cylindrical outer surface. The throttle element is at least partially encapsulated by means of the thermally conductive body and thus at least partially encased and/or enclosed by the thermally conductive body with surface contact. This encapsulation can be configured in very different ways. For example, the thermally conductive body can have a channel-like recess into which the throttle element, tightly enclosed by the thermally conductive body, is pushed and/or fitted. Alternatively, the throttle element can be encapsulated by a material which, in the hardened state, forms the thermally conductive body. Preferably, the thermally conductive body is at least substantially, preferably completely, not made from plastic. Preferably, the heat-absorption surface is larger than the outer surface of the throttle element by at least a factor of 2, preferably by a factor of 5, and particularly preferably by a factor of greater than 10.

In one embodiment of the invention, the throttle element is encapsulated completely in the thermally conductive body. "Completely" means that the throttle element is in full-surface contact with the thermally conductive body along its entire length and about its entire circumference. This contact naturally excludes regions of the throttle element that serve for the entry and/or exit of the fluid-line channel extended partially through the throttle element. A further improved heat transfer between the thermally conductive body and the throttle element can be achieved by this embodiment of the invention. Ultimately, this enables an improved heat transfer from the skin surface to the throttle element. In this way, undesired temperature fluctuations at the throttle element can be counteracted still more effectively.

In a further embodiment of the invention, the throttle element is made from at least a first material, and the thermally conductive body is made from at least a second material which has a higher coefficient of thermal conduction than the first material. By this choice of material, a further improved heat transfer from the skin surface to the throttle element can be achieved. In particular, compared to a conceivable enlargement simply of the outer surface of the throttle element and direct bearing of said outer surface on the skin surface, this embodiment of the invention permits a considerable improvement in the heat transfer.

In a further embodiment of the invention, the thermally conductive body is made from a metal and/or a thermally conductive ceramic. It has proven particularly advantageous here to use aluminum and/or copper. Particularly suitable as the thermally conductive ceramic are aluminum oxide and/or aluminum nitride. A particularly high coefficient of thermal conduction of the thermally conductive body can be achieved by this embodiment of the invention.

In a further embodiment of the invention, the thermally conductive body is designed in the form of a thermally conductive pad, which has a flexible pad-shaped envelope and a liquid and/or gel-like thermally conductive medium encased in a fluid-tight manner by the envelope. Compared to the other dimensions of the thermally conductive pad, the pad-shaped envelope is preferably designed with a thin wall. The envelope can be made, for example, from a flexible plastic, from a textile configured to be fluid-tight, or similar.

To encase the thermally conductive medium, individual portions of the pad-shaped envelope can be adhesively bonded or sewn to each other or joined together in some other way. The thermally conductive medium can in particular be a paste, a cream, a gel or a liquid. By virtue of the flexible nature of the envelope, on the one hand, and the liquid and/or gel-like thermally conductive medium, on the other hand, the shape and/or configuration of the thermally conductive pad is conformable. In this way, the heat-absorption surface can be applied particularly easily and with the correct contouring to the skin surface. This ensures that the contact between the skin surface and the heat-absorption surface is as complete as possible, which permits yet further improvement in the heat transfer. Moreover, this provides improved wearing comfort by comparison with a thermally conductive body that is not conformable in shape.

In a further embodiment of the invention, the heat-absorption surface is provided with an adhesive layer. The adhesive layer serves to apply the thermally conductive body to the skin surface. By means of the adhesive layer, it is possible to dispense with separate application of sticking plaster and/or dressing material in order to apply the thermally conductive body to the patient.

In a further embodiment of the invention, the fluid-line channel is encapsulated in the thermally conductive body in a region that adjoins the throttle element upstream in relation to a direction of flow of the medical fluid. This adjoining region can also be designated as a pre-heating region. The encapsulation of the pre-heating region in the thermally conductive body has the effect that the medical fluid is already pre-heated before entering the throttle element. By means of the medical fluid already being heated before it enters the throttle element, temperature-related influences on the throttle action can be further reduced. Since the pre-heating region adjoins the throttle element upstream, it is ensured that the medical fluid is pre-heated in only a limited region. This is important in particular for temperature-sensitive medical fluids.

For the medical elastomeric pump mentioned at the outset, the object of the invention is achieved by the fact that a medical fluid-line arrangement according to the above description is provided which, at the inlet side, is connected in a fluid-conducting manner to the outlet of the pump volume.

BRIEF DESCRIPTION OF THE DRAWING FIGURES

Further advantages and features of the invention will become clear from the following description of preferred exemplary embodiments of the invention, which are explained with reference to the drawings.

DETAILED DESCRIPTION

Figure 1:
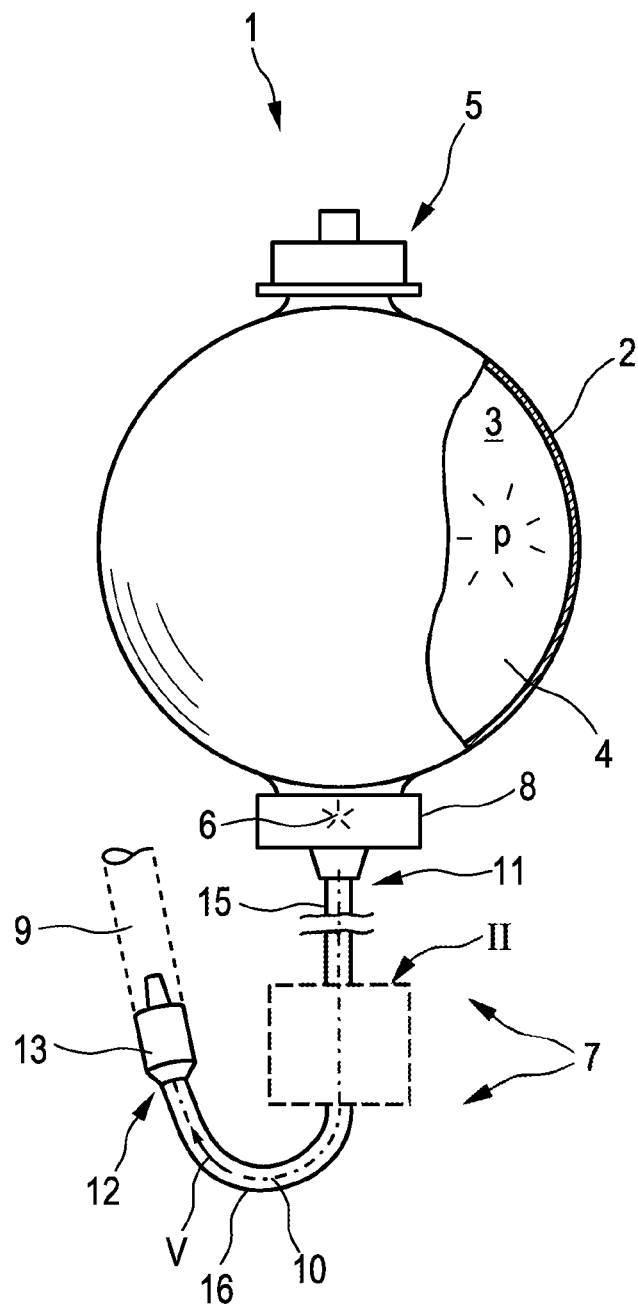
FIG. 1 shows, in a greatly simplified schematic view, an embodiment of a medical elastomeric pump according to the invention, at the outlet of which an embodiment of a medical fluid-line arrangement according to the invention is connected in a fluid-conducting manner.

According to FIG. 1, a medical elastomeric pump 1 is provided for use in outpatient and/or inpatient infusion therapy. The medical elastomeric pump 1 serves to receive and deliver a medical fluid 4 and can also be designated as an elastomeric infusion pump.

The medical elastomeric pump 1 has an elastomeric membrane 2 which forms a pump volume 3 for receiving and delivering the medical fluid 4. In the present case, the medical fluid is a liquid medicament 4 not defined in any more detail. With reference to FIG. 1, the medical elastomeric pump 1 is shown in a filling state. In this filling state, the pump volume 3 is filled with the medical fluid 4, as a result of which the elastomeric membrane 2 is flexibly expanded like a balloon on account of a mechanical action of the medical fluid 4. In FIG. 1, the elastomeric membrane 2 is illustrated with an exaggerated wall thickness for graphic reasons. By contrast, in an unfilled state, the elastomeric membrane 2 is slack or at any rate less elastically expanded. For filling the pump volume 3 with the medical fluid, a reclosable filling nozzle 5 is provided, which is attached to the membrane 2 in a fluid-tight manner known in principle. The elastic expansion of the elastomeric membrane 2 subjects the pump volume 3 to a delivery pressure p, by means of which the medical fluid 4 can be delivered through an outlet 6 of the pump volume 3 into a medical fluid-line arrangement 7 that is connected in a fluid-conducting manner to the outlet 6. As will also be seen from FIG. 1, the outlet 6 of the pump volume 3 is arranged in the region of a passage nozzle 8 which, at an end region of the elastomeric membrane 2 directed away from the filling nozzle 5, is attached to said elastomeric membrane in a fluid-tight manner known in principle.

The medical fluid-line arrangement 7 is only shown in a greatly simplified and partially cut-away schematic view in FIG. 1. The medical fluid-line arrangement 7 serves to transfer the medical fluid 4 from the pump volume 3 of the elastomeric pump 1 to a patient port 9, which is only indicated symbolically in the drawing. In order to transfer the medical fluid 4, the fluid-line arrangement 7 has a fluid-line channel 10, indicated by a dot-and-dash line. The fluid-line channel 10 has an inlet 11 and an outlet 12. In the present case, the inlet 11 is secured non-releasably on the passage nozzle 8 and is connected to the outlet 6 in a fluid-conducting manner. In an embodiment not shown, the inlet 11 can be provided with a suitable connector for releasable fluid-conducting connection to the elastomeric pump 1. In the present case, the outlet 12 leads into a connector 13, which is provided for fluid-conducting connection to the patient port 9. The connector 13 is a Luer connector in the present case, but this is not obligatory. In an embodiment not shown, the connector 13 can be designed for example in the form of an attachment marketed under the federally registered trademark NRFit®. By means of the delivery pressure p, the medical fluid 4 is thus able to be delivered from the pump volume 3 into the inlet 11 of the fluid-line channel 10 via the outlet 6 and can be delivered therefrom further through the outlet 12 into the patient port 9 via the connector 13.

In the present case, the medical elastomeric pump 1 is dimensioned in such a way that it can be readily worn on the body by a patient and can be used without an external energy supply, particularly in the context of outpatient therapy. The medical elastomeric pump 1 is accordingly light and dimensionally compact, wherein in the present case the pump volume 3 has a nominal size of 400 ml. It goes without saying that the pump volume 3 may also differ from this, for example having a nominal size of between 50 ml and 750 ml.

Figure 2:
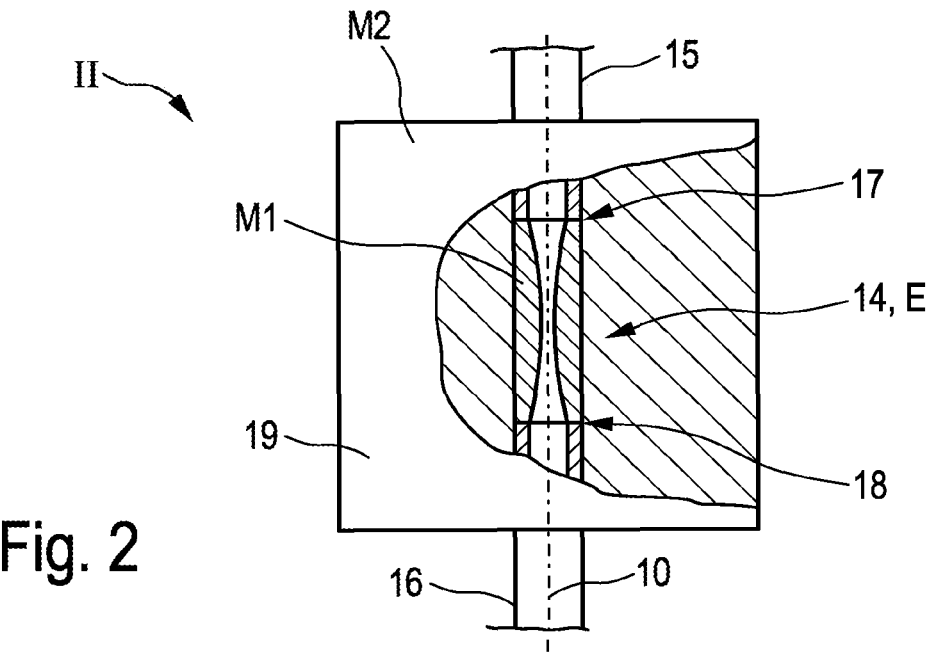
FIG. 2 shows, in a partially cut-away and sectional enlarged detail, a region II of the fluid-line arrangement according to FIG. 1.
Figure 3:
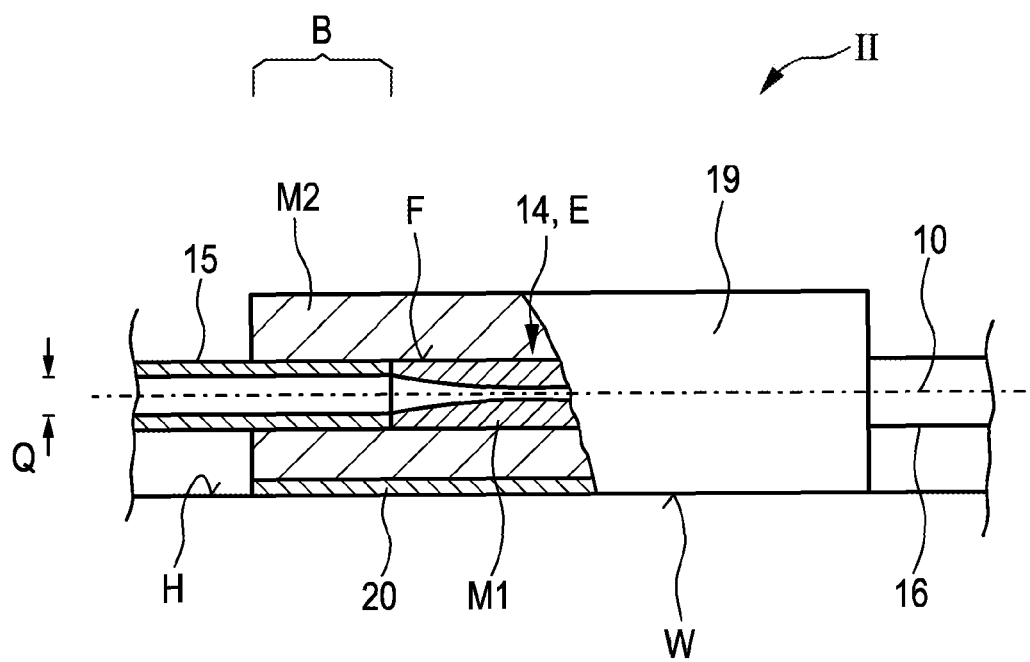
FIG. 3 shows the region according to FIG. 2 in a partially cut-away and sectional side view.

It will be seen from FIGS. 2 and 3 that the fluid-line arrangement 7 moreover has a throttle element 14 which is connected to the inlet 11 and to the outlet 12 in a fluid-conducting manner. In this respect, the fluid-line channel 10 extends at least partially through the throttle element 14. In FIGS. 2 and 3, this can be seen from the dot-and-dash lines shown in these for illustrating the fluid-line channel 10. The throttle element 14 causes a partial narrowing E of an active-flow cross section Q of the fluid-line channel 10. The throttle element 14 serves to throttle a volumetric flow V of the medical fluid 4 that is delivered through the fluid-line channel 10 by means of the elastomeric pump 1.

In the present case, the throttle element is designed in the form of a capillary element 14 and is made from plastic. Moreover, the throttle element 14 can also be designated as a flow limiter.

In the present case, the fluid-line channel 10 is formed from an arrangement of a plurality of line portions 15, 16 and the throttle element 14. In the present case, the line portions are each designed in the form of a flexible hose portion 15, 16 made from plastic. The hose portion 15 adjoins the throttle element 14 upstream in relation to a delivery direction of the volumetric flow V as indicated in FIG. 1. The hose portion 16 adjoins the throttle element 14 downstream. An outlet (not shown in detail) of the hose portion 15 is connected in a fluid-conducting manner to an inlet 17 of the throttle element 14. By contrast, an inlet (not shown in detail) of the hose portion 16 is connected in a fluid-conducting manner to an outlet 18 of the throttle element 14. For this purpose, the hose portions 15, 16 and the throttle element 14 can be joined together in a manner known in principle. In an embodiment not shown, it is instead possible to simply provide a hose portion which extends continuously between inlet 11 and outlet 12 and on which a throttle element is integrally formed.

The fluid-line arrangement 7 moreover has a thermally conductive body 19. The throttle element 14 is encapsulated at least partially in the thermally conductive body 19. Compared to an outer surface F, the thermally conductive body 19 has a larger heat-absorption surface W which is intended to be applied flat to a skin surface H of a patient (FIG. 3).

The thermally conductive body 19 serves to transfer body heat from the skin surface H to the throttle element 14. This is primarily intended to counteract temperature fluctuations on the throttle element 14. Such unwanted temperature fluctuations can lead to a change of viscosity of the medical fluid 4 in the region of the throttle element and thus to a change of the throttle action thereof. Fluctuations of the volumetric flow V can thereby arise, which can ultimately have a negative effect on the overall administration of the medical fluid 4. The thermally conductive body 19 and the design of the rest of the fluid-line arrangement 7 counteract this.

In the present case, the throttle element 14 has a circular cylindrical outer contour. The outer surface F is therefore, in the present case, the lateral surface of a circular cylinder. In the present case, the thermally conductive body 19 has a cuboid shape, which is to be understood purely as an example. The heat-absorption surface W is many times larger than the outer surface F. In an exemplary embodiment not shown, the heat-absorption surface W can be at least one order of magnitude larger than the outer surface F. The thermally conductive body 19 encases the throttle element 14 such that an inner wall (not shown in detail) of the thermally conductive body 19 is in planar contact with the outer surface F. In the present case, the throttle element 14 is encapsulated completely in the thermally conductive body 19, except for the regions joined together at the ends to the hose portions 15, 16.

In the present case, the throttle element 14 is made from at least a first material M1. The thermally conductive body 19 is made from at least a second material M2. Compared to the first material M1, the second material M2 has a higher coefficient of thermal conduction. The first material M1 is in the present case a plastic not defined in any more detail. The second material M2 is a metal. In the present case, the metal chosen is aluminum. In an embodiment not shown, the metal chosen can be copper, for example. In another embodiment not shown, the thermally conductive body can be made from a thermally conductive ceramic, for example from aluminum oxide and/or aluminum nitride.

To apply the heat-absorption surface W to the skin surface H, an adhesive layer 20 is provided in the present case. The adhesive layer 20 is arranged on the underside of the thermally conductive body 19. In a state (not shown) in which the fluid-line arrangement 7 is supplied, the adhesive layer 20 can be provided with a cover film or the like, which prevents unwanted adhesion of the adhesive layer 20 and can be removed from the adhesive layer 20 before the thermally conductive body 19 is applied. The adhesive layer 20 does not necessarily have to be provided. In order to apply the thermally conductive body 19 to the skin surface H, it is instead possible to use sticking plaster and/or dressing material or to position it beneath a layer of clothing of the patient, for example, although this is less advantageous.

As can be seen in particular from FIG. 3, the fluid-line channel 10 is encapsulated in the thermally conductive body 19 in a region B that adjoins the throttle element 14 upstream in relation to the direction of the volumetric flow V. In this way, the medical fluid 4 can be warmed even before it enters the throttle element 14. The region B can thus also be designated as a pre-heating region. A length of the pre-heating region B is advantageously dimensioned such that the volumetric flow V is already heated to a maximum achievable temperature when it enters the throttle element 14. For this purpose, in particular the length of the pre-heating region B, the other dimensions of the thermally conductive body 19, the thermal conduction properties of the second material M2 and the heat-absorption surface W have to be coordinated with one another, taking account of the volumetric flow V.

Figure 4:
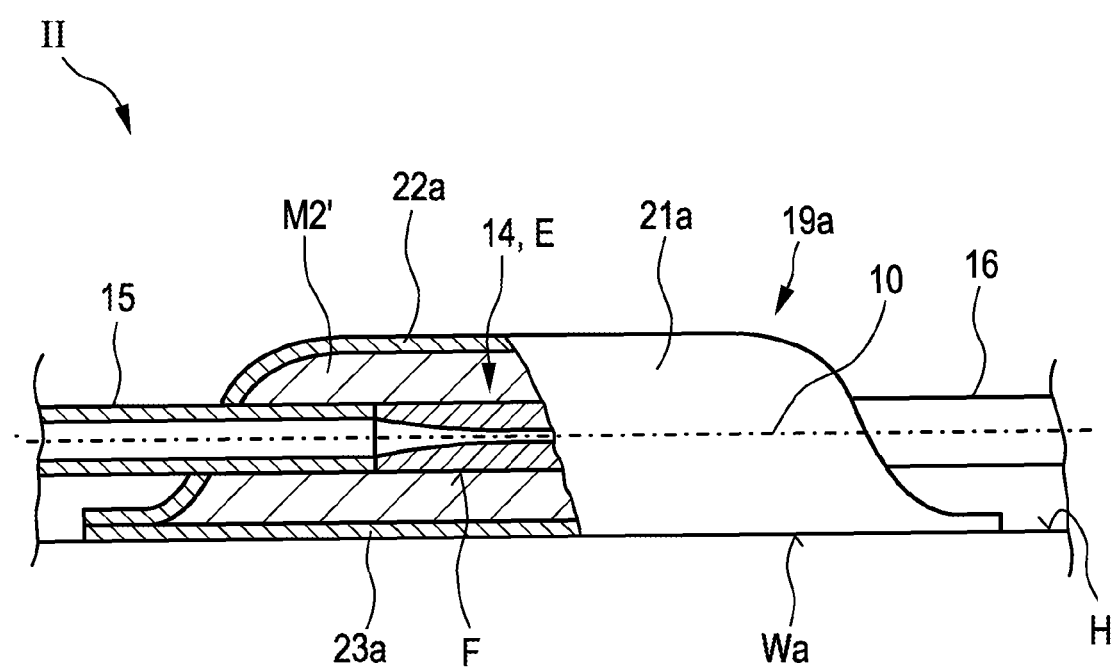
FIG. 4 shows a further embodiment of a medical fluid-line arrangement according to the invention in a region II according to FIG. 1 and in an illustration according to FIG. 3.

FIG. 4 shows a further embodiment of a fluid-line arrangement according to the invention, the view being limited to the region II according to FIG. 1. The fluid-line arrangement according to FIG. 4 differs from the embodiment described with reference to FIGS. 1 to 3 only in terms of the design of the thermally conductive body 19a shown in FIG. 4. In this respect, structural parts and portions of identical design are labeled with identical reference signs and are not separately described again. Instead, in order to avoid repetition, reference is made to the disclosure concerning the fluid-line arrangement 7 according to FIGS. 1 to 3, which disclosure, apart from the design of the thermally conductive body 19a, applies correspondingly for the embodiment according to FIG. 4.

The thermally conductive body that can be seen in FIG. 4 is designed in the form of a thermally conductive pad 19a. The thermally conductive pad 19a has a flexible pad-shaped envelope 21a and a second material in the form of a liquid and/or gel-like thermally conductive medium M2'. The thermally conductive medium M2' is encased in a fluid-tight manner in the envelope 21a. By virtue of the flexible nature of the pad-shaped envelope 21a and the liquid and/or gel-like state of the thermally conductive medium M2', the shape of the thermally conductive pad 19a is conformable. It is thereby possible, firstly, to achieve a particularly advantageous flat application of the whole heat-absorption surface Wa on the skin surface H. Secondly, the conformability enhances the wearing comfort.

In the present case, the pad-shaped envelope 21a is made from a film that is made of a plastic not defined in detail. In the present case, the envelope 21a has an upper portion 22a and a lower portion 23a in relation to the drawing plane of FIG. 4, said portions 22a, 23a being joined together in a fluid-tight manner at the edge. For example, the portions 22a, 23a can be adhesively bonded to each other, sewn together or joined in a fluid-tight manner in some other way.

In the present case, the thermally conductive medium M2' is a gel not defined in any more detail. The gel M2' lies over the entire outer surface F of the throttle element 14. In the present case, an entire volume of the envelope 21a is filled by the gel M2', such that no air inclusions remain. Moreover, the envelope 21a is attached in a fluid-tight manner to an outer circumference of the hose portion 15 and to an outer circumference of the hose portion 16, in a way that is not shown in any detail, such that in these attachment regions too there is no escape of the thermally conductive medium M2' from the envelope 21a.

It will be appreciated that the underside of the thermally conductive pad 19a can be provided with an adhesive layer 20 (cf. FIG. 3) in the region of the heat-absorption surface Wa.

The invention claimed is:

1. A medical fluid-line arrangement for transferring a medical fluid between a medical elastomeric pump and a patient port, the medical fluid-line arrangement comprising:
   a fluid-line channel with an inlet for connection in a fluid-conducting manner to a pump outlet of the medical elastomeric pump, and an outlet for connection in a fluid-conducting manner to the patient port; and
   a throttle element comprising a portion of the fluid-line channel, the throttle element being connected in a fluid-conducting manner to the inlet of the fluid-line channel and to the outlet of the fluid-line channel such that an entire flow from the inlet of the fluid-line channel to the outlet of the fluid-line channel passes through the throttle element, wherein the throttle element comprises a throttle element body having an outer surface and an inner passage, the inner passage comprising:
      a throttle element inlet having a first cross-sectional area,
      a throttle element outlet having a second cross-sectional area, and
      a throttle element central region extending fluidly between the throttle element inlet and the throttle element outlet, the throttle element central region consisting of a single throttle passageway through which the entire flow from the inlet of the fluid-line channel to the outlet of the fluid-line channel passes, the single throttle passageway having a third cross-sectional area, wherein the third cross-sectional area is less than the first cross-sectional area and the second cross-sectional area to thereby create a partial narrowing of a cross section of the fluid-line channel at the single throttle passageway,
   wherein the throttle element body is completely encapsulated in a thermally conductive body, wherein the thermally conductive body serves to transfer body heat from a skin surface of a patient to the throttle element and has a heat-absorption surface that is larger than the outer surface of the throttle element body and that is intended to be applied flat to the skin surface of the patient;

wherein the thermally conductive body comprises a thermally conductive pad having a flexible pad-shaped envelope and a liquid and/or gel-like thermally conductive medium encased in a fluid-tight manner by the flexible pad-shaped envelope.

2. The medical fluid-line arrangement according to claim 1, wherein the throttle element is made from at least a first material, and the thermally conductive body is made from at least a second material which has a higher coefficient of thermal conduction than the first material.

3. The medical fluid-line arrangement according to claim 1, wherein the thermally conductive body further comprises a metal material and/or a thermally conductive ceramic material.

4. The medical fluid-line arrangement according to claim 1, wherein the heat-absorption surface comprises an adhesive layer.

5. The medical fluid-line arrangement according to claim 1, wherein a portion of the fluid-line channel located between the inlet of the fluid-line channel and the throttle element inlet is encapsulated in the thermally conductive body.

6. A medical elastomeric pump for delivering a medical fluid, the medical elastomeric pump comprising:

a medical fluid-line arrangement according to claim 1; and an elastomeric membrane which forms a pump volume for receiving and delivering the medical fluid, wherein the elastomeric membrane is elastically expanded in a filling state at least partially filled with the medical fluid and exerts an expansion-induced delivery pressure on the pump volume, wherein a volumetric flow of the medical fluid is deliverable through an outlet of the pump volume by the expansion-induced delivery pressure, and wherein the medical fluid-line arrangement is connected at an inlet side to the outlet of the pump volume in a fluid conducting manner.

7. The medical fluid-line arrangement according to claim 1, wherein the throttle element central region comprises a capillary passage.

8. The medical fluid-line arrangement according to claim 1, wherein the flexible pad-shaped envelope comprises a lower portion defining the heat-absorption surface, and an upper portion extending from a perimeter of the heat-absorption surface, and wherein fluid-line channel passes through and is attached in a fluid-tight manner to the upper portion at a location spaced from the heat-absorption surface.

9. The medical fluid-line arrangement according to claim 1, wherein the liquid and/or gel-like thermally conductive medium completely surrounds the outer surface of the throttle element body.

10. The medical fluid-line arrangement according to claim 1, wherein the third cross-sectional area is less than the first cross-sectional area and the second cross-sectional area by at least one order of magnitude.

11. The medical fluid-line arrangement according to claim 1, wherein the third cross-sectional area is less than the first cross-sectional area and the second cross-sectional area by at least two orders of magnitude.

12. The medical fluid-line arrangement according to claim 1, wherein the outer surface of the throttle element body is cylindrical.

13. The medical fluid-line arrangement according to claim 1, wherein the heat-absorption surface has a first surface area and the outer surface of the throttle element body has a second surface area, and the first surface area is greater than the second surface area by at least a factor of 5.

14. The medical fluid-line arrangement according to claim 1, wherein the heat-absorption surface has a first surface area and the outer surface of the throttle element body has a second surface area, and the first surface area is greater than the second surface area by at least one order of magnitude.

15. The medical fluid-line arrangement according to claim 1, wherein the throttle element has a first fluid resistance and a remainder of the fluid-line channel has a second fluid resistance, and the first fluid resistance is greater than the second fluid resistance by at least one order of magnitude.

16. The medical fluid-line arrangement according to claim 1, wherein the throttle element has a first fluid resistance and a remainder of the fluid-line channel has a second fluid resistance, and the first fluid resistance is greater than the second fluid resistance by at least two orders of magnitude.

* * * * *